United States Patent [19]

Kornberg

[11] Patent Number: 4,489,133
[45] Date of Patent: Dec. 18, 1984

[54] TWO-DIMENSIONAL CRYSTALLIZATION TECHNIQUE

[75] Inventor: Roger D. Kornberg, Atherton, Calif.

[73] Assignee: The Board of Trustees of the Leland Stanford Jr. University, Stanford, Calif.

[21] Appl. No.: 442,066

[22] Filed: Nov. 16, 1982

[51] Int. Cl.$^3$ .............................................. B32B 9/00
[52] U.S. Cl. ..................................... 428/408; 428/420; 428/478.2; 427/2; 435/7; 378/73; 424/88; 260/112 R; 260/112 B
[58] Field of Search .............. 435/7; 378/73; 428/420, 428/478.2, 408; 427/2

[56] References Cited

U.S. PATENT DOCUMENTS 4,172,827  8/1975  Gigeuer ................................ 424/88

Primary Examiner—Sam Silverberg
Attorney, Agent, or Firm—Bertram I. Rowland

[57] ABSTRACT

Methods and compositions involving two-dimensional ordering of organic polar solvent soluble organic macromolecules. Lipid monolayer forming molecules are bound covalently or non-covalently to organic macromolecules soluble in polar solvents, whereby the macromolecules are allowed to become oriented in two-dimensions to form an ordered, low free energy, including crystalline, layer of macromolecules. The macromolecules may then be further combined with other moieties to create additional layers, to be cross-linked or otherwise modified, and/or separated from the lipid monolayer. The resulting ordered layers can be used for a variety of purposes, in crystallographic techniques for structure determination and structural relationship determinations, in optics, as polymers, films, and the like.

10 Claims, No Drawings

TWO-DIMENSIONAL CRYSTALLIZATION TECHNIQUE

BACKGROUND OF THE INVENTION

1. Field of the Invention

Many organic molecules may be crystallized or oriented, if at all, only laboriously and frequently with only partial success. The ability to orient or crystallize a wide variety of molecules readily could open up new areas of insight into molecular structure as well as new applications for these molecules.

One area of interest is the study of structure and structural relationship between molecules. For example, antibodies and enzymes are interesting receptor molecules whose structure and relationship with their ligands is of substantial scientific interest which could lead to practical applications. However, these molecules and their complexes with their respective ligands have often proved intransigent in the preparation of samples for X-ray crystallography.

Crystallization also imparts properties to compositions which are not available to the composition in the non-crystalline state. Crystallized or oriented molecules, can find use in optics, electronics, as structural elements, and the like.

2. Description of the Prior Art

Non-specific adsorption and hexagonal ordering of ferritin was reported by Fromberg, Nature (1971) 231:267–268. Hexagonal patches of ferritin also form on a carbon source in the absence of a lipid monolayer. Feder and Giaever, J. of Colloid and Interface Science (1980) 78:144–154. C&EN, Oct. 4, 1982, page 19 describes the use of a monolayer for oriented polymerization of alkynylcarboxylic acids.

SUMMARY OF THE INVENTION

Molecules are bound, either covalently or non-covalently, to the polar end of monolayer forming surfactants and permitted to orient themselves in a low free energy state, providing an ordered array of the molecules. Particularly, organic macromolecules may be employed. The resulting ordered layer can serve as a template to provide additional ordered layers, can be modified, cross-linked, and/or separated from the lipid monolayer and may be used as samples in X-ray crystallography, or as the active component in a variety of applications.

DESCRIPTION OF THE SPECIFIC EMBODIMENTS

Novel layers or laminations are provided by employing lipid monolayer forming molecules to orient molecules of interest. The lipid molecules provide reversible means for joining to the molecule of interest, so that ultimately the lipid may be separated from the ordered array of the molecules of interest. The molecules of interest are limited to those which can be joined, covalently or non-covalently to the lipid molecules, have the necessary solubility in a polar medium, and are capable of forming ordered two-dimensional arrays.

The method involves forming a monolayer of the lipid, contacting the monolayer with the molecule of interest in a polar medium at an appropriate concentration and allowing sufficient time for the molecule of interest (hereinafter referred to as the "lyend") to assume a low free energy state, providing for an ordered array, including crystalline, of the lyend. Depending upon the purpose of the ordered array, as well as the nature of the lyend, additional molecules may be added which interact with the lyend so as to form an additional layer, whereby laminations can be built up providing low free energy ordering of the layers.

The materials involved in the subject invention are the lipid surfactant monolayer forming material, the lyend, which may involve secondary or subsequent order lyends, the polar solvent, additives to the polar solvent, and particular materials for special applications.

The lipid monolayer forming material will involve a lipid chain (the lipophilic region), a polar group (the hydrophilic region), and a moiety for binding, either covalently or non-covalently, but usually reversibly, to the lyend. The lipid portion will generally be a hydrocarbon chain of from about 8 to 24 carbon atoms, more usually of from about 8 to 18 carbon atoms, which may be saturated or unsaturated and there may be from 1 to 4 such chains per molecule. The lipid groups are conventional finding extensive description in the prior art for forming monolayers, liposomes, as constituents in naturally occurring membranes, and the like. The polar group may be non-ionic or ionic, including anionic and cationic. Various groups include phosphates, phosphate esters, carboxylate, amino, quaternary ammonium, sulfate, sulfonate, hydroxyl, mercapto, etc. One or more of these groups may be used together, as one or more lipid groups may be present in the same molecule.

Illustrative lipids include phospholipids, such as phosphatidyl surfactants e.g. phosphatidyl choline, phosphatidyl inositol and phosphatidyl ethanolamine; cardiolipin, lecithin, sphingomyelin, cerebrosides, gangliosides, etc. See U.S. Pat. No. 4,193,983, for a description of conjugating molecules to lipids and for a description of ligands and receptors.

The group for joining the surfactant to the lyend will be present at the polar end of the surfactant and will depend upon the nature of the lyend. Where covalently reversible bonding is desired, the disulfide bond is particularly useful, where the lipid surfactant and the lyend each have a thio group which can be joined by oxidation. Other groups which can be cleaved chemically include such molecules as the hydrazo, imino, ester, etc. The hydrazo group can be alkylated with halogen and then cleaved by reduction. The imino group can be formed between an oxo group and an amino or hydrazine group, and then cleaved by treatment with mild acid. Esters can be readily formed from carboxyl groups activated with carbodiimide. The ester may then be readily hydrolyzed using either mild acid or base. These illustrations are not exhaustive, but merely illustrative of a few of the more common procedures for forming groups which may then be cleaved to restore two molecules, normally the original two molecules.

Where non-covalent bonding is desired, ligand-receptor non-covalent bonding can be employed. A wide variety of ligands may be involved, such as haptens, biotin, substrates, and coenzymes. Lectins can be used with sugars, etc. Also, complementary nucleotide sequences may be employed using either RNA or DNA with a small complementary oligonucleotide bound to the surfactant, usually of about 8 to 30 bases.

A single or mixture of lipids may be used for forming the monolayer, depending upon the nature of the lyend, the nature of the lipid, the desired degree of packing of the lyend, and the like. Typically, there will be 5–50 mol % of the lipid surfactant capable of joining to the lyend.

The lyend is limited by only a few considerations. Normally, the lyend will have a molecular weight of at least about 1,000, more usually at least about 2,000, and will generally be 5,000 or more. For the most part, the lyend will be an organic molecule, but can include metallo- organic molecules, organosilanes, etc. The lyend must also have sufficient solubility in a polar solvent which allows for monolayer formation of the lipid surfactant. For the most part, the solvent that is employed will be aqueous solvents which may include a wide variety of organic solvents in combination. Usually, the organic solvent will not exceed 60 vol. %, more usually not exceeding about 40 vol. %. Various water miscible solvents may be employed, such as alcohols e.g. methanol and ethanol, amides e.g. N,N-dimethyl formamide, ketones e.g. acetone, etc. Water miscibility is not required, and other organic solvents may find use in particular situations, which organic solvents have only moderate water solubility.

One class of lyend compounds of particular interest are the poly(amino acids). The poly(amino acids) are exemplified by polypeptides and proteins. A wide variety of poly(amino acids) have receptor activity, such as antibodies, e.g. IgG, IgM, IgA, IgG and IgE, enzymes, and naturally occurring receptors e.g. avidin, cell surface receptors and histones. Where the poly(amino acid) does not have receptor activity, functionalization may be required, such as introduction of an available mercapto group or utilization of mercapto groups which are available on the molecule. Alternatively, the poly(amino acid) may be bound to a natural receptor e.g. avidin, antibody, etc.

Another category of compounds of interest are polynucleotides or nucleic acids, which may include DNA or RNA, where the DNA may be chromosomal, extrachromosomal, plastid e.g. chloroplast or mitochondrial, viral, etc., or RNA, such as messenger RNA, transfer RNA, ribosomal, synthetic, etc. By employing an oligonucleotide as a ligand bound to the lipid, one can bind to nucleic acid sequences having a complementary sequence. These will then be oriented in two-dimensions to form an ordered array of nucleotide sequences of the same composition.

Other kinds of compounds can also be used as the lyend. Exemplary compounds include metalloorganics, such as heme, chlorophyll, various oxidases, and the like.

The lyend layer may serve as a basis for the formation of second or multiple monomolecular layers. For example, with antibodies, Clq, Rf, *S. aureus* protein A, or other specific receptor can be added which will bind to the antibody. Alternatively, one can modify the antibody to provide for further binding, by conjugating a hapten to the antibody different from the hapten to which the antibody binds. Lectins may find use with sugars to provide additional layers. The lyend may serve as a ligand for additional receptors to provide a layer of a receptor. Various compositions may be employed for the variety of applications in which the subject invention may be used.

In carrying out the subject invention, one prepares a monolayer. The monolayer may be at an air-water or organic solvent-water interface or may be removed from the interface and bound to a hydrophobic surface e.g. carbon. Once the monolayer has formed, the monolayer is contacted with the lyends in an aqueous medium. Usually, mild temperatures are employed, generally ranging from 0° to 50° C. Depending upon the nature of the lyend, the solution may be buffered, stabilizers may be added, or other additives to provide for ionic strength, viscosity, or the like. In some instances, by varying the additive, one may be able to vary the conformation of the lyend, so as to provide for a different final product. The combination of lipid surfactant and lyend is allowed to stand for a sufficient time for ordering to occur. In some situations, it may be desirable to cycle the temperature or otherwise alter the solution conditions to enhance the crystallinity of the system.

The concentration of the lyend will vary widely and may range from several $\mu$g to several mg per ml.

It will frequently be desirable to prepare the monolayer bound to a carbon or other hydrophobic surface and then contact the monolayer with the lyend solution. After a sufficient time, the support surface may be withdrawn.

In some instances, it may be desirable that the lyend be fixed in its relationship with adjacent lyend molecules. Cross-linking can occur by the use of high energy radiation, various cross-linking agents, or the like. With poly(amino acids) cross-linking agents can include formaldehyde, various bifunctional reagents, tanning agents and the like. With nucleic acids, nucleic acids can be cross-linked with psoralens, diazotizing reagents, and the like.

In order to demonstrate the subject invention, the following experiments were carried out. The purpose of the experimentation was to prepare electron micrographs of ordered arrays of antibodies on lipid monolayers. Silver grids were used to avoid corrosion problems. The grids were coated with collodion, carbon and a lipid monolayer and were floated on drops of antibody solution in microtiter wells at room temperature. After the grids were withdrawn and washed with several drops of water, they were negatively stained with 1% uranyl acetate. The antibody was purified from ascites fluid by precipitation with ammonium sulfate, chromatography on QAE-Sephadex and gel filtration through Sephadex G200.

The layers were formed as follows. The monolayer was formed by spreading a few drops of the lipid in hexane solution on an air-water interface in a Teflon trough. The electron microscope grid, freshly coated with carbon, was passed through the interface, resulting in the deposition of a lipid monolayer with the hydrocarbon chains abutting the hydrophobic carbon surface and the polar head groups facing the aqueous solution. The surface of the trough was swept free of lipid and the grid was withdrawn into air and transferred to a drop of antibody solution.

In one experiment, linear arrays of anti-dinitrophenyl antibodies on a dinitrophenyl-phosphatidyl ethanolamine monolayer were produced after 10 hrs. exposure to 250 $\mu$g/ml of antibody in 150 mM sodium chloride, 50 mM Tris, pH 8.1. In a second experiment, the lipid monolayer composition was modified employing a 1:1 mole ratio mixture of the above lipid and phosphatidly choline.

In the first experiment, the pattern observed in the electron microscope was a linear pattern which could be observed within 1 to 3 hrs. of incubation. The linear patterns are characterized by stain-excluding stripes with a lateral spacing or center-to-center distance of 150±10 Å. Each stripe is itself divided down the middle by a thin line of stain and at high magnification the stripes show transverse lines or striations with spacing of approximately 40 Å. This image is readily interpreted in terms of the packing of IgG molecules with both Fab arms bound to the lipid monolayer and the Fc tail projecting into solution. The stripes correspond to rows of molecules stacked with Fab-Fc-Fab planes flat against one another. The striations correspond to individual antibody molecules viewed in projection down their Fc tails. The spacings of the stripes and striations are in good agreement with the corresponding molecular dimensions of 142 and 50 Å from X-ray crystallography.

When the above experiment was carried out, except employing a concentration of antibody at 50 μg/ml and an incubation of 15 hrs. exposure, hexagonal arrays of the antibodies were observed. The hexagonal array is a crystalline structure characterized by a hexagonal system of large stain-excluding elements with a spacing (center-to-center distance) of 150±10 Å. The extent of the ordered regions was not large, but the degree of order within a region was high. Optical diffraction from such regions gave patterns that could be indexed on a hexagonal lattice. The diffraction extended to at least four orders, corresponding to a resolution of about 60 Å.

A further experiment was carried out whereby the antibodies were complexed with Clq. For the complexation, the DNP-PE coated grid was exposed to antibodies (50 μg/ml) for 8 hrs. and then to excess Clq for a further 10 hrs, as in the first experiment. The resulting electron micrograph showed both linear and hexagonal arrays. The regions of hexagonal ordering were similar in size and quality to those found with antibody alone, but on image processing, a significant difference emerged. The antibody lattice decorated with Clq showed a striking alternation in stain exclusion from one large element of the array to the next. The difference between adjacent elements was 6 contour levels out of 18. In contrast with antibody alone, the difference was never greater than 1 level out of 18. Clq binding affects the staining pattern of the trimer clustered Fab arms, rather than that of the Fc tails.

The above data evidences the use of the subject invention in providing for linear arrays and crystal formation of compounds which cannot readily be crystallized. Thus, the subject invention can be used to provide new compositions of matter which can be used not only for the study of chemical structure but also in optical systems, as diffraction grids and filters, as catalysts, for electrical transmission, as films, polymers, and the like.

Chromophores, such as dyes and fluorescers e.g. biliproteins, chlorophyll, hemoglobin, etc., may be oriented to act as polarizers, filters, fluorescers, antennaes and the like.

The subject invention provides for a simple and rapid way to prepare crystalline structures of single molecular layers of a wide variety of organic compounds, as well as multilayered laminates. The method has both use in the investigation of compounds, and the production of novel products which find wide application.

Although the foregoing invention has been described in some detail by way of illustration and example for purposes of clarity of understanding, it will be obvious that certain changes and modifications may be practiced within the scope of the appended claims.

What is claimed is:

1. A method for ordering molecules in a lower free energy state as a monomolecular layer, wherein said molecules are characterized by being at least partially soluble in a polar medium, capable of forming an ordered array, capable of binding to a surfactant having lipophilic and hydrophilic regions, wherein said surfactant includes means for binding to said molecule in said hydrophilic region;

said method comprising:
combining under binding conditions a solution of said molecules in a polar solvent with a monolayer of said surfactant situated at about the surface of said solution, whereby said molecules bind to said surfactant; and
incubating the mixture for a time sufficient to allow for ordering of said molecules as a monomolecular layer.

2. A method according to claim 1, wherein said monolayer of surfactant is bound to a solid surface.

3. A method according to any of claims 1 or 2, wherein said molecules are macromolecules of at least about 5,000 molecular weight.

4. A method according to claim 3, wherein said molecules are poly(amino acids).

5. A method according to claim 3, wherein said molecules are polynucleotides and said means is an oligonucleotide.

6. A method according to claim 3, including the additional step of combining said monolayer of molecules with a solution of second molecules in a polar solvent, and incubating the mixture for a sufficient time for said second molecules to bind to said molecules as an ordered second monomolecular layer of second molecules.

7. A method for orienting organic receptors in a lower free energy state as a monomolecular layer, wherein said receptors are members of a specific binding pair consisting of ligand and receptor, by employing surfactants having lipophilic and hydrophilic regions and ligand bound to said surfactant in said hydrophilic region;

combining a solution of said receptors in a polar medium under ligand-receptor binding conditions with a monolayer of said surfactant situated at about the surface of said solution;
incubating the mixture for a sufficient time for said receptors to bind to said ligand and assume an ordered array as a monomolecular layer.

8. A method according to claim 7, wherein said receptors are antibodies.

9. A composition prepared according to claim 1.

10. A composition prepared according to claim 7.

* * * * *

UNITED STATES PATENT AND TRADEMARK OFFICE
CERTIFICATE OF CORRECTION

PATENT NO. : 4,489,133
DATED      : December 18, 1984
INVENTOR(S) : ROGER D. KORNBERG It is certified that error appears in the above-indentified patent and that said Letters Patent is hereby corrected as shown below:

Column 1, line 6, insert the following:

--This invention was made with Government support under NIH Grant No. CA24546. The Government has certain rights in this invention.--

Signed and Sealed this

Twenty-ninth Day of November, 1994

Attest:

BRUCE LEHMAN

Attesting Officer     Commissioner of Patents and Trademarks